(12) United States Patent
Bornzin et al.

(10) Patent No.: US 7,359,752 B1
(45) Date of Patent: Apr. 15, 2008

(54) CONFIGURABLE TEST LOAD FOR AN IMPLANTABLE MEDICAL DEVICE

(75) Inventors: Gene A. Bornzin, Simi Valley, CA (US); Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 313 days.

(21) Appl. No.: 11/181,708

(22) Filed: Jul. 13, 2005

(51) Int. Cl.
*A61N 1/00* (2006.01)
(52) U.S. Cl. ....................................................... 607/27
(58) Field of Classification Search ................ 607/27; 600/510
See application file for complete search history.

(56) References Cited

U.S. PATENT DOCUMENTS 5,237,991 A * 8/1993 Baker et al. .................. 607/27
5,314,452 A   5/1994 Hirschberg et al. ........... 607/36

* cited by examiner

*Primary Examiner*—Carl Layno
*Assistant Examiner*—Brian T Gedeon

(57) ABSTRACT

A test assembly for an implantable medical device, which includes a patient simulator capable of providing signals to the implantable medical device that are representative of the patient's organ function to thereby test whether the implantable medical device is capable of detecting circumstances requiring the deliver of therapy. The patient simulator further includes a plurality of loads that can be selected to correspond to the loads actually seen by the implantable medical device when delivering therapy to the patient.

18 Claims, 6 Drawing Sheets

CONFIGURABLE TEST LOAD FOR AN IMPLANTABLE MEDICAL DEVICE

FIELD OF THE INVENTION

The invention relates to implantable medical devices and, in particular, concerns a configurable test load device which can be used in conjunction with implantable medical device to assist the ability of the implantable medical device to deliver stimulation therapy to a patient either prior to or during implantation of the implantable medical device.

BACKGROUND OF THE INVENTION

Implantable medical devices come in a variety of configurations. Devices such as pacemakers, implantable cardioverter/defibrillators (ICD) or cardiac stimulation devices incorporating both the functionality of pacemakers and ICDs are commonly used devices that provide stimulation therapy to a patient in order to regulate heart function. Implantable cardiac stimulation devices can generally apply a variety of different electrical waveforms to the patient in order to treat various different arrhythmias that affect heart function. Preferably, at implantation, it is desirable to be able to test the implantable medical device to ensure that the implantable medical device will deliver appropriate therapy to the patient.

Hence, at implantation various testing procedures have been implemented with implantable medical devices to assess their ability to deliver appropriate therapy to the patient. For example, at implantation of an ICD, it is common for the physician to induce fibrillation of the heart to ensure that the ICD will detect the fibrillation and will also apply the appropriate stimulation to the heart to terminate the fibrillation. Naturally this procedure is not without some risk as the ICD may either be unable to detect or terminate the fibrillation. At that point, an external defibrillator is typically used in order to termination the fibrillation.

Due to the risks associated with testing implantable cardiac stimulation devices, there has been a need for systems that test the implantable cardiac stimulation device without posing substantial risk to the patient. Some examples of external testing devices are disclosed in U.S. Pat. No. 5,237,991 to Baker Jr. et al. and also in U.S. Pat. No. 5,314,452 to Hershberg et al. These types of devices typically include a fixed resistive load that is positioned across the output terminals of the cardiac stimulation device. The device can then be induced to produce a cardiac stimulation waveform and the results of the waveform can then be assessed typically using delimited data that is transmitted to an external programmer.

While these devices reduce the risk associated with having the implantable cardiac stimulation device attempt to terminate a particular arrhythmia at implantation, these devices have several shortcomings. Initially, these devices typically only use a single fixed load which is often not representative of the actual load of the heart when therapy is actually being applied. This is particularly problematic for implantable cardiac stimulation devices which have a capability of applying a variety of different defibrillation, cardioversion or pacing waveforms to different regions of the heart to correct various arrhythmias. Moreover, simply positioning a fixed load across the output terminals of an implantable cardiac stimulation device only tests the ability of the device to deliver a waveform but does not provide any indication as to the ability of the implantable device to detect various arrhythmias. Consequently, these types of devices generally do not reduce the need to test the device on the actual patient with all of the inherent risks.

In some circumstances, many physicians may be unwilling to test the device on the patient on implantation due to the inherent risks. For example, advanced pacing devices may also include high voltage capability that can provide either cardioversion or defibrillation waveforms to the heart. If the patient has never exhibited previous symptoms that would require the delivery of high-voltage waveforms, the treating physician may be unwilling to test the ability of the device to deliver these waveforms to the patient due to the risk. Consequently, if the patient does subsequently exhibit an arrhythmia that requires a high voltage waveform, the device may be unable to provide the waveform and this inability of the device would have gone undetected.

From the foregoing, it should be appreciated that there is a need for a system that is capable of assessing the ability of an implantable medical device to detect circumstance that require the delivery of therapeutic stimulation to a patient without requiring the device to be tested on the patient itself. To this end, there is a need for a device which more accurately simulates the patient and can also be configured to test not only the ability of the implantable medical device to deliver therapeutic waveforms, but also the ability of the device to sense the existence of a circumstance which would require the delivery of the therapeutic waveforms.

SUMMARY

The aforementioned needs are satisfied by the invention which, in one aspect, comprises a configurable patient simulator that can be remotely configured to simulate a plurality of different loads representative of a plurality of different locations within the patient's body to which the implantable medical device will deliver stimulation. In this way, implantable medical devices, such as pacemakers and ICDs, can be tested to determine their ability to deliver a variety of different waveforms to a variety of different locations.

In another aspect of the invention, the patient simulator also has the ability to output signals to the sensor inputs of the implantable medical device that simulate the medical condition for which the implantable medical device is configured for delivering therapy. For example, the patient simulator can be configured to deliver a signal that is representative of ventricular fibrillation to an input of an implantable cardiac stimulation device. This functionality thus allows the device to be tested as to whether it will recognize the occurrence of the ventricular fibrillation and also whether it will able to deliver an appropriate waveform in response to detecting the simulated existence of ventricular fibrillation.

From the foregoing, it will be appreciated that the patient simulator of the present invention is capable of more realistically simulating conditions within the patient's body. Moreover, the patient simulator is not only able to test the ability of the implantable device to deliver therapy, but is also able to test the ability of the implantable medical device to detect when therapy is to be delivered to the patient. As a consequence, the patient simulator of the present invention provides a more realistic assessment of the ability of the implantable medical device to deliver therapeutic waveforms to the patient and thus reduces the need for the implantable medical device to actually be tested on the patient with all of the inherent risks at implantation. These and other objects and advantages of the present invention

DETAILED DESCRIPTION

Reference will now be made to the drawings for like numerals refer to like parts throughout. The following description includes the best mode presently contemplated for practicing the invention. This description is not to be taken in a limiting sense but is made merely for the purpose of describing the general principles of the invention. The scope of the invention should be ascertained with reference to the issued claims. In the description that follows, like numerals or reference designators will be used to refer to like parts or elements throughout.

Figure 1:
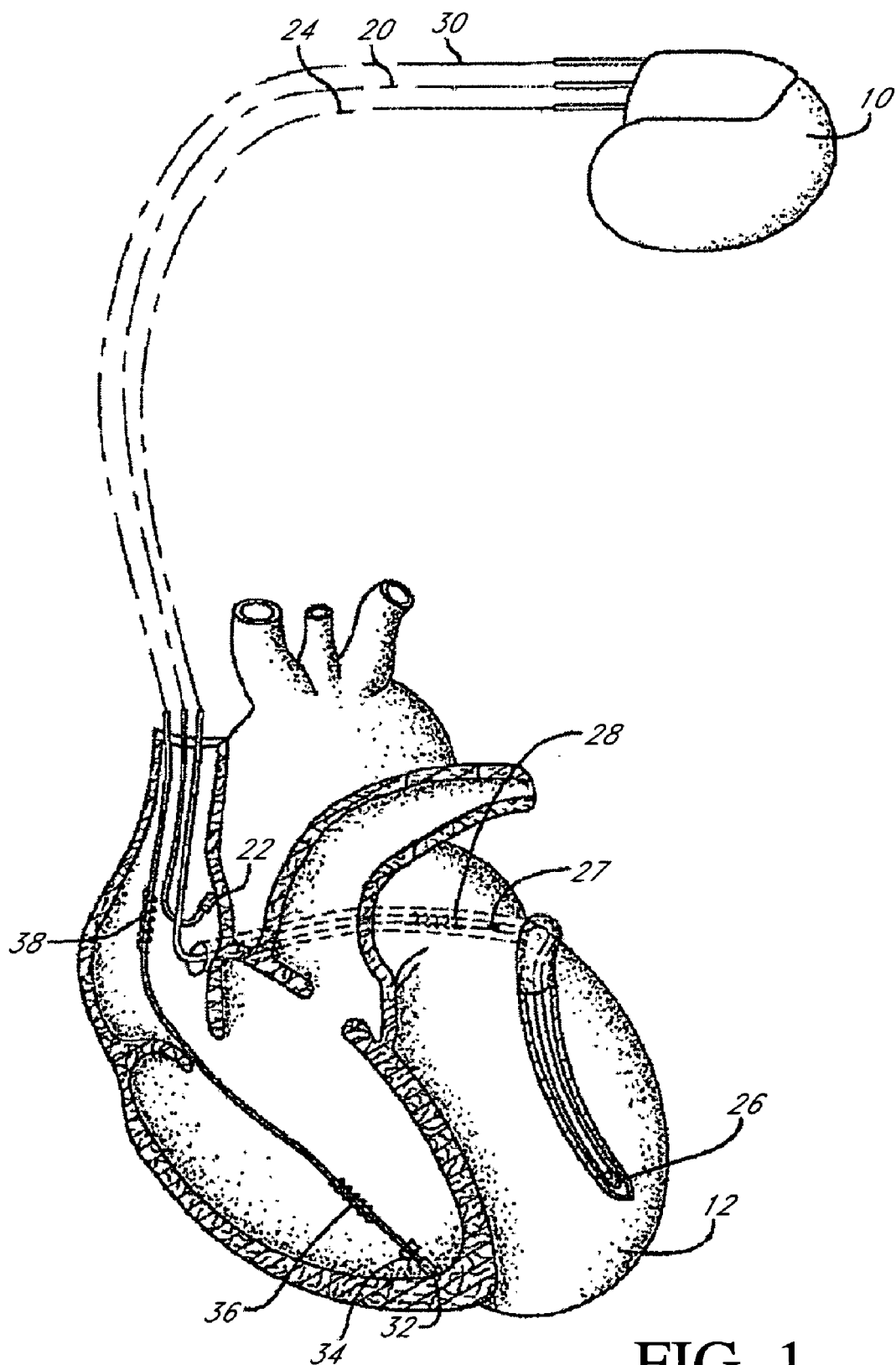
FIG. 1 is a schematic illustration illustrating the physical components of an implantable cardiac stimulation device as it is implanted to provide therapy to the heart of a patient.

As shown in FIG. 1, there is a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
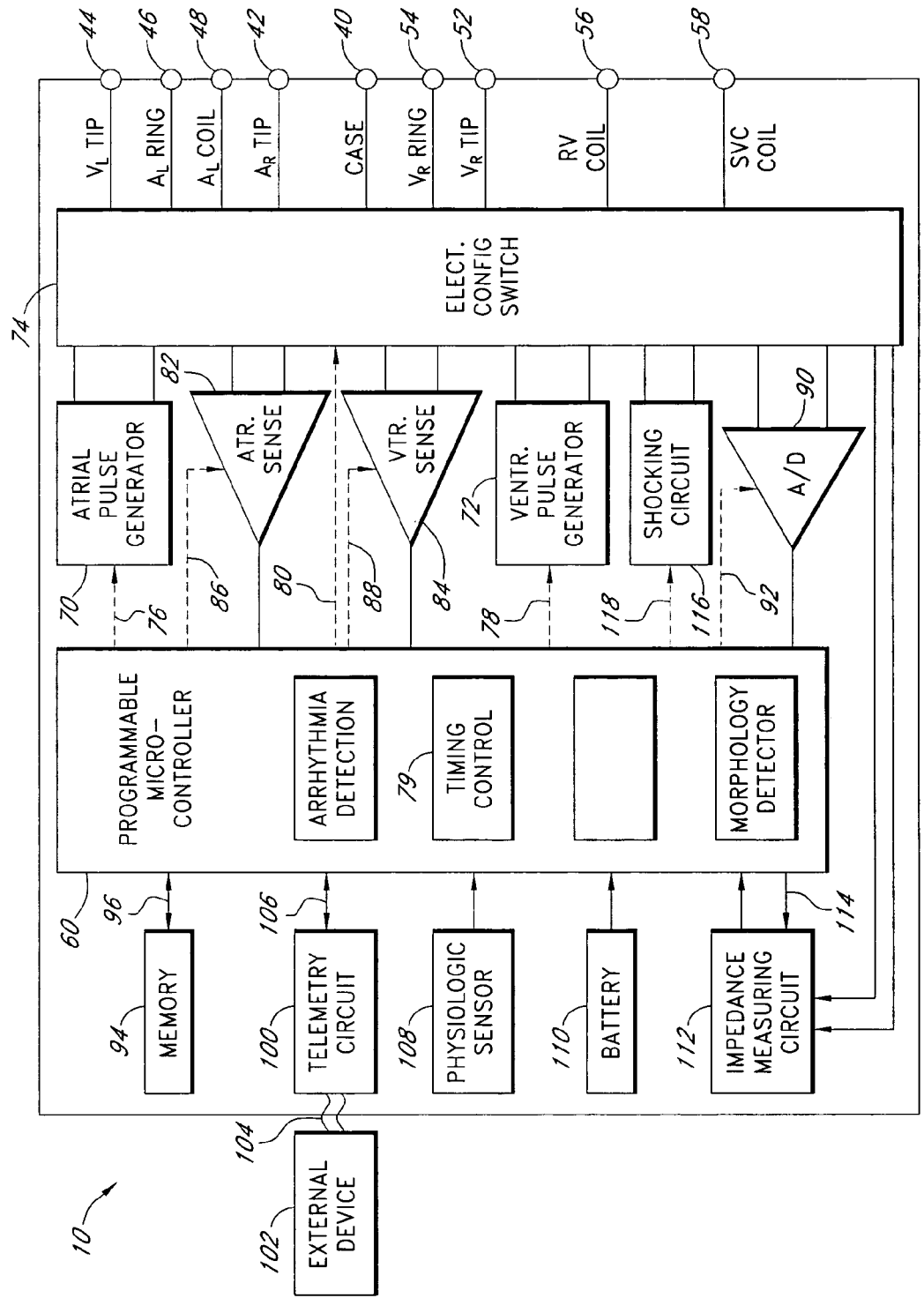
FIG. 2 is a simplified schematic illustration of the implantable cardiac stimulation device of FIG. 1.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

A housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein.

The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated independent pulse generators, multiplexed pulse generators, or shared pulse generators. The pulse generators 70 and 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30 through the switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit 82 and 84 preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits 82 and 84 are connected to the microcontroller 60 which, in turn, are able to trigger or inhibit the atrial and ventricular pulse generators 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators 70 and 72 generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all)

current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes and, as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The foregoing description has described an exemplary implantable cardiac stimulation device 10 which incorporates the functionality of both a pacemaker and an ICD. As discussed previously, it is often desirable to be able to test the functionality of the implantable cardiac simulation device 10 and, in particular, the capability of the implantable cardiac stimulation device 10 to detect a condition for which there are people who can be provided and also to assess the ability of the implantable cardiac stimulation device to deliver one or more therapeutic waveforms. As will be discussed in greater detail below, the test assembly of the illustrated embodiment includes a patient simulator which allows for testing of the implantable cardiac stimulation device prior to implantation, thus not requiring the implantable cardiac stimulation device to be tested on the patient. While the following description will describe the test assembly in connection with an implantable cardiac simulation device 10, such as the device 10 described above, a person of ordinary skill in the art will appreciate that any of a number of implantable medical device that sense the patient's body function and provides therapy in response to the sense function can be used in connection with an appropriately configured test assembly and patient simulator without departing from the spirit of the present invention.

Figure 3:
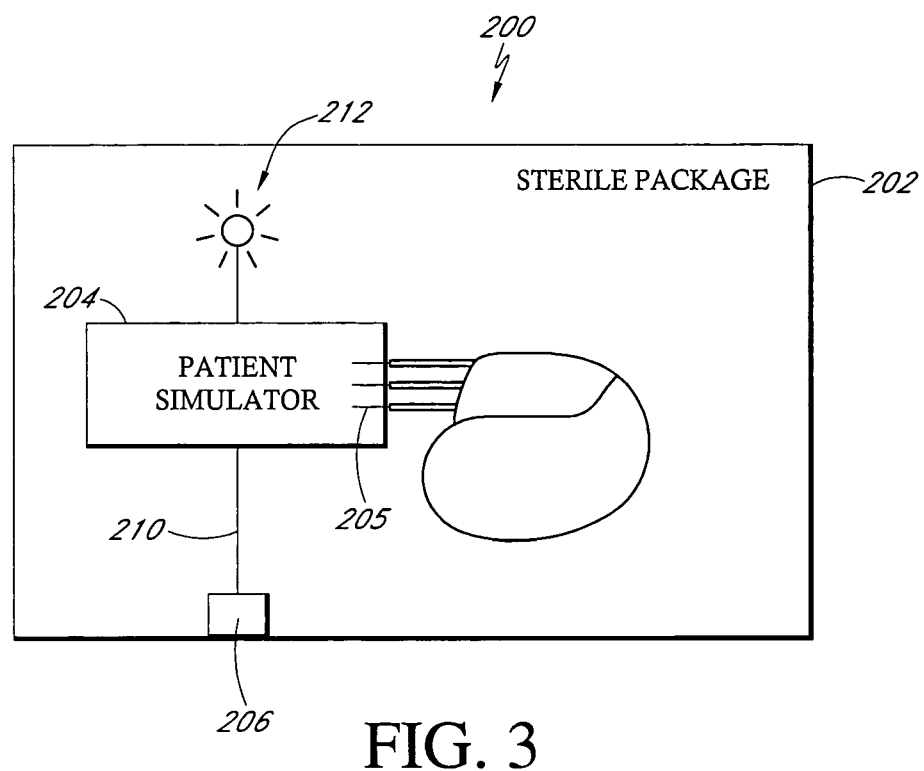
FIG. 3 is a block diagram illustrating a first embodiment of a test assembly for testing an implantable medical device.

Referring specifically to FIG. 3, an exemplary test assembly 200 is illustrated. As shown in FIG. 3, the test assembly 200 includes the implantable cardiac stimulation device 10 which is connected to a patient simulator 204 via inputs 205. Preferably, the implantable cardiac stimulation device 10 and the patient simulator 204 are positioned within a sterile barrier or package 202 and are shipped as a single unit to the location where the implantation is to occur. Positioning the simulator 204 and the implantable cardiac stimulation device 10 within the sterile package 202 allows for testing of the implantable cardiac stimulation device 10 with reduced risk of contamination of the device 10 prior to implantation.

As is illustrated in FIG. 3, the test assembly 200 further includes the communications link 210 which, in this embodiment, is comprised of a hardware communications link having an external port 206 which is suitable for connection to a monitoring system, such as an external programmer, in a manner that will be described in greater detail below. Moreover, as will also be described in greater detail below, the patient simulator 204 is capable of providing signals to the implantable cardiac stimulation device 10 to induce the cardiac stimulation device 10 to generate and apply waveforms to the patient simulator 204 and is further capable of capturing data indicative of the waveform and the operation of the device 10. As is also illustrated in FIG. 3, the test assembly 200 also includes an annunciator 212 which provides a visual indication of the delivery of a waveform by the implantable cardiac stimulation device 10.

Figure 4:
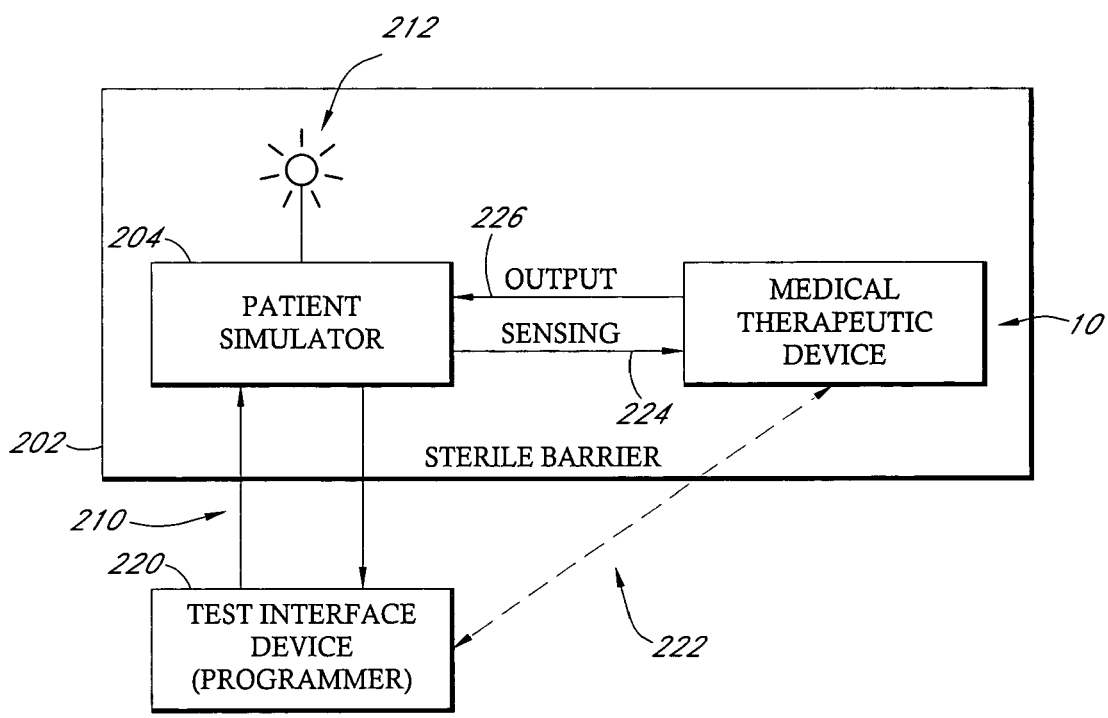
FIG. 4 is a block diagram of a second embodiment of a test assembly for testing implantable medical device.

FIG. 4 is a block diagram which functionally illustrates the operation of the test assembly 200 in greater detail. In particular, the patient simulator 204 is in communication via a communication link 210 with a test interface device 220. The communication link 210 between the test interface device 220 and the patient simulator 204 may be the hard wired configuration as is shown in FIG. 3 or, alternatively, may be an RF link or other remote link that communicates through the sterile package 202.

The test interface device 220 may comprise an external programmer that is adapted to communicate not only with the implantable medical device 10 via a telemetry link 222, but also with the patient simulator 204 via the telemetered link 210. Preferably, the test interface device 220 can induce the patient simulator 204 to send appropriate signals to the medical therapeutic device via the sensing link 224. These signals are generally signals that are modeled after the signals that the device 10 would receive when implanted.

For example, the signal output by the patient simulator 204 on the sensing output 224 may initially comprise an IEG signal indicative of normal sinus rhythm that an implantable cardiac stimulation device would receive via the lead(s) in the manner described above. The signal can then change into an abnormal IEG signal that would be indicative of an arrhythmia, such as ventricular fibrillation, atrial fibrillation, or the like. Alternatively, the abnormal IEG signal may be a signal indicative of the heart needing a pacing pulse from the device 10.

Preferably, the implantable cardiac stimulation device 10 upon receiving the abnormal IEG signal would detect the change in the IEG signal and then develop and apply an appropriate waveform or pacing pulse via the output channel 226 to the patient simulator 204. As will be described in greater detail below, the patient simulator 204 includes a configurable load which can be configured to simulate the load on the implantable cardiac stimulation device 10 when the particular therapeutic stimulation is being applied. It will be appreciated that the load will typically vary depending upon the electrodes from which the therapy is to be delivered and thus the locations of the heart to which the therapy is to be delivered. By having a configurable load, the patient simulator 204 can simulate any of a number of arrhythmias or other conditions that the implantable cardiac stimulation device 10 may have to treat when implanted in the patient. The patient simulator 204 can then provide signals to the test interface device 220 indicative of the waveform that had been delivered by the implantable cardiac stimulation device 10 and can also provide a visual indication of the delivery of a waveform via the visual annunciator 212.

Figure 5:
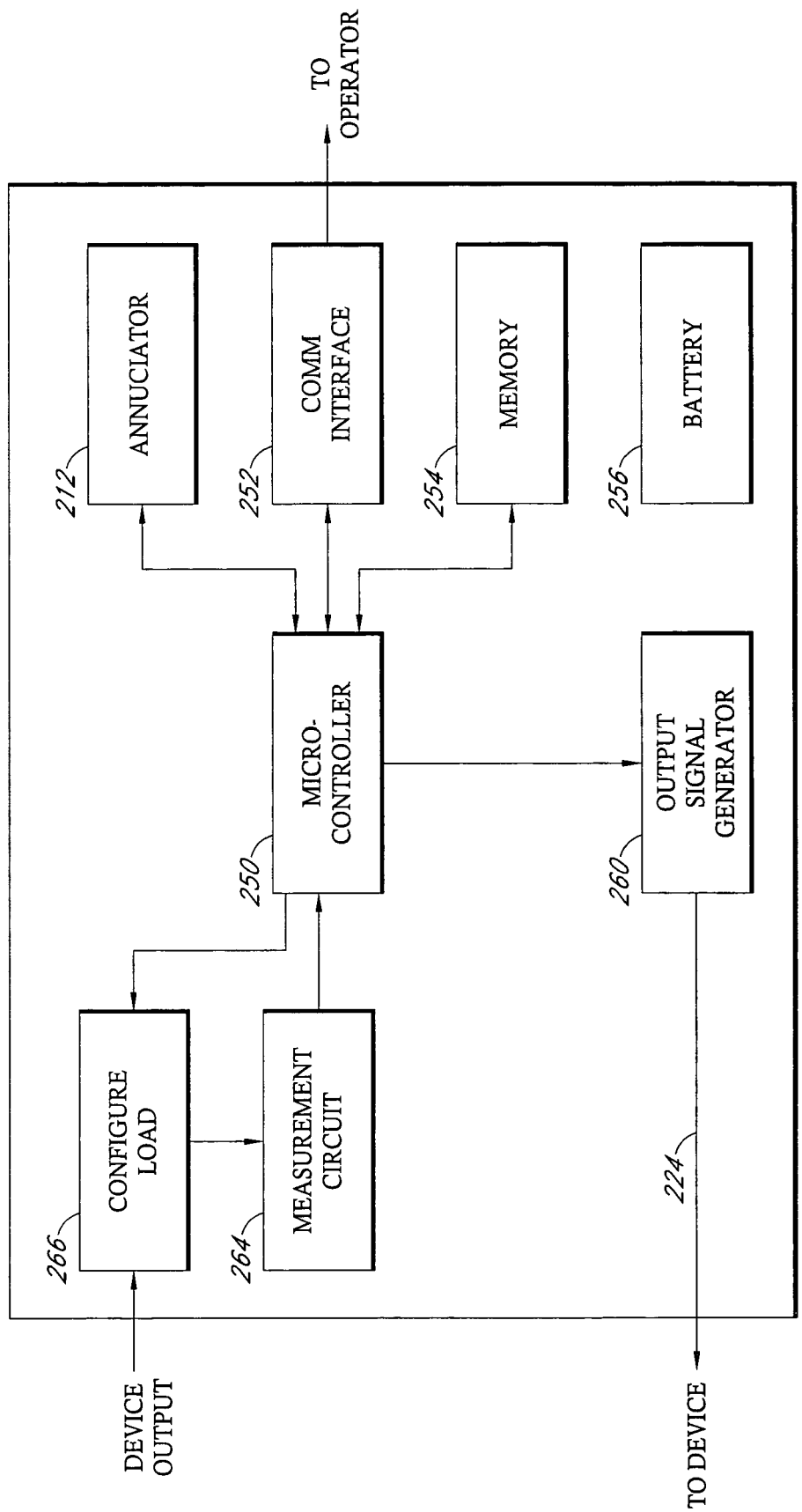
FIG. 5 is a block diagram of a patient simulator which forms a portion of the test assembly of either FIG. 3 or 4.

FIG. 5 is a block diagram which illustrates the functional components of the patient simulator 204. As indicated, the patient simulator 204 includes a microcontroller 250 which can be any of a number of well-known microprocessors programmed to implement the functionality described herein. Power is supplied to the simulator from a battery 256 in a known manner. The microcontroller 250 has an associated memory 254 in which program instructions and data can be stored and retrieved by the microcontroller 250. The microcontroller 250 further sends signals to an output signal generator 260 so as to generate the signals to be sent to the implantable cardiac stimulation device 10 via the communication link 210 to simulate the signals that the implantable cardiac stimulation device 10 would receive from the patient when implanted.

The microcontroller 250 is further capable of sending and receiving signals from the test interface device 220 via a communications interface 252. As discussed above, the communications interface 252 can comprise either an RF telemetry communications interface of the type commonly used with implantable cardiac stimulation devices and external programmers or can be a hardwired interface such as the one described above in connection with FIG. 3.

As is also illustrated in FIG. 5, the microcontroller 250 can also send signals to an annunciator 212 to provide either a visual or audible indication of the delivery of a waveform. However, as will be described in greater detail below, the annunciator 212 can also be directly coupled to a load that is to receive the output waveform from the implantable cardiac stimulation device 10 and thereby provide a visual indication of the magnitude of the delivered therapy.

As is also illustrated in FIG. 5, the patient simulator 204 further includes a configurable load 266 that is configurable in response to signals from the microcontroller 250 so as to simulate the electrical load that a particular electrode of the implantable cardiac stimulation device 10 would see when delivering therapy to the patient in response to a detected arrhythmia. As will be described in greater detail below, the configurable load 266 includes both resistive and capacitive and/or inductive elements so as to more accurately simulate the actual electrical load characteristics of the various target regions of the heart 12 during the delivery of therapeutic electrical waveforms or pacing pulses following implantation.

As is also illustrated in FIG. 5, a measurement circuit 264 is associated with the configurable load 266 such that the waveform delivered to the configured load can be measured and stored and subsequently sent to the test interface device 220 to thereby allow implanting medical personnel to assess the performance of the implantable cardiac stimulation device 10 prior to implantation. As indicated in FIG. 5, the configurable load 266 and measurement circuit 264 in combination with the microcontroller 250 comprise an adjustable measurement component 262 that is described in greater detail in FIG. 6.

Figure 6:
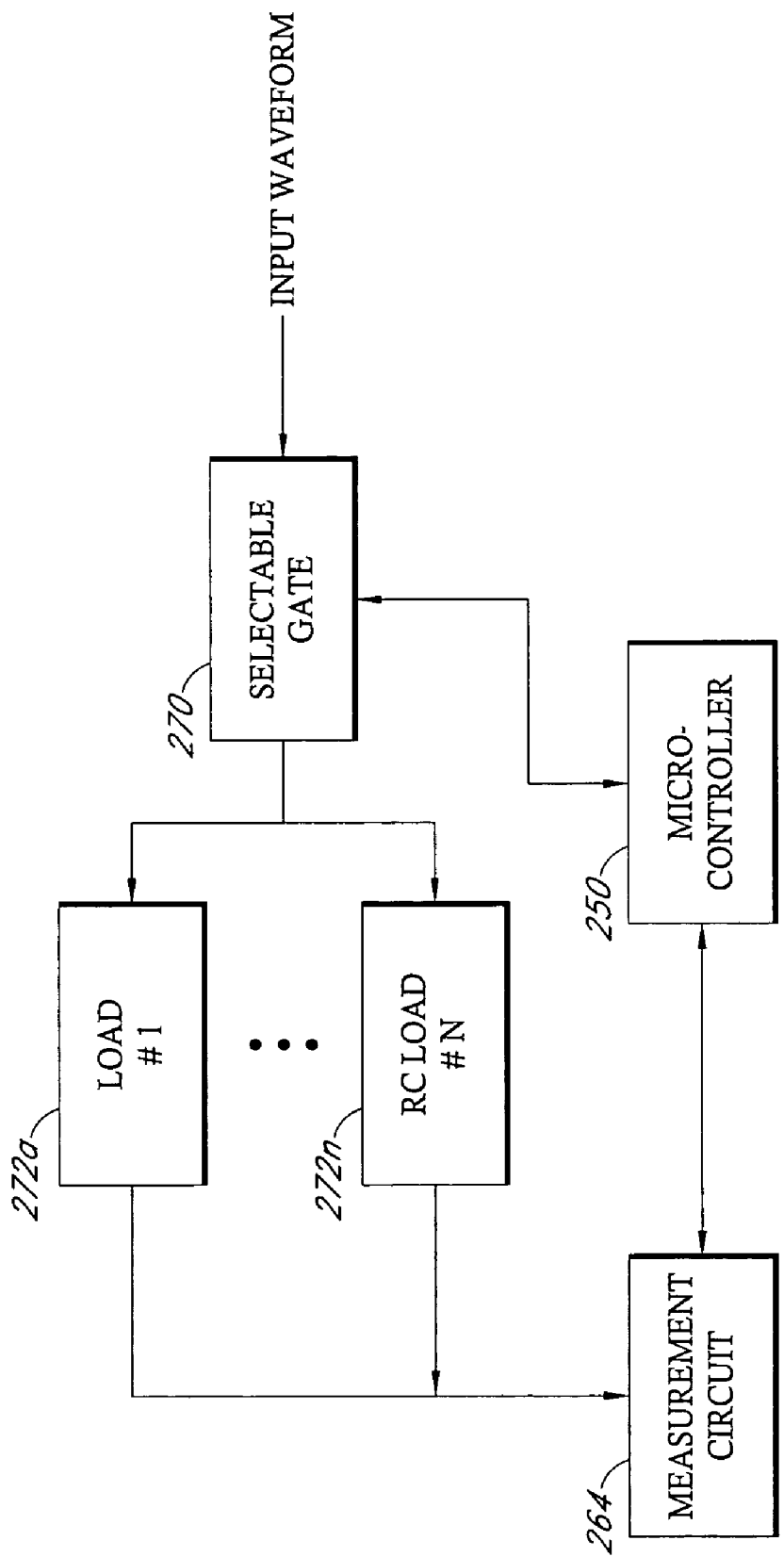
FIG. 6 is a block diagram illustrating the components of the patient simulator of FIG. 5 which simulates a variety of different loads and captures measurement data indicative of a waveform delivered by the implantable medical device.

FIG. 6 is a functional block diagram illustrating one possible functional or logical organization of the adjustable measurement component 262 of the patient simulator 204. As shown, the microcontroller 250 sends signals to a selectable gate 270 which can comprise any of a number of devices including multiplexers and the like, wherein the waveform or other output provided by the implantable cardiac stimulation device is directed to one or more loads 272a-272n. Preferably, the loads 272a-272n include both resistive and capacitive or inductive components as the actual electrical load characteristics of the heart during delivery of a pacing pulse or therapeutic waveform typically also include a resistive and capacitive and/or inductive components. The loads 272a-272n are selected to correspond to the electrical load that would be seen by a particular electrode when delivering a particular therapeutic electrical stimulation.

For example, one of the loads may comprise a load that simulates the electrical load seen by the pacing tip 26 (FIG. 2) when pacing pulses are being delivered. Similarly, another one of the loads may simulate the electrical load that the implantable cardiac stimulation device 10 would see when delivering a bi-phasic high voltage defibrillation waveform via a coil electrode positioned within the ventricle of the patient's heart. Various other loads may be representative of the load that the implantable cardiac stimulation device 10 would see when delivering pacing, cardioversion or defibrillation therapy to any of the chambers of the heart. Hence, the microcontroller 250, by manipulating the selectable gate 270, can send the waveform from the implantable cardiac stimulation device to any of a number of loads 272a-272n that more accurately simulate the actual conditions or load that the implantable cardiac stimulation device 10 would see when applying therapy to the heart of the patient.

Once the waveform from the implantable cardiac stimulation device 10 has been directed to a particular load 272a-272n, the measurement circuit 264 captures data about the waveform as it is applied to the selected load 272a-272n and provides data about the waveform to the microcontroller 250. By capturing data about the waveform, the microcontroller 250 can then transmit the waveform data to the test interface device 220 via the communications interface 210 in the manner described above. The captured data can include a digital sampling of the waveform that illustrates the peak power delivered to the heart as well as the duration of the waveform. The exact configuration of the data can, of course, vary based upon implementation. This would allow an implanting treating medical professional to evaluate the waveform that is being delivered by the implantable cardiac stimulation device 10 to assess whether the implantable cardiac stimulation device 10 is suitable for implantation into the patient.

Hence, the patient simulator 204 not only is capable of sending signals to the implantable cardiac stimulation device 10 to test whether the cardiac stimulation device 10 is capable of detecting the occurrence of an arrhythmia, it also has a number of different loads 272a-272n which can be selected so as to more closely correspond to the actual loads the device 10 would see when delivering any of a number of different stimulation therapies to the heart 12 of the patient. Thus, the patient simulator of the illustrated embodiment provides for more flexible testing of the implantable cardiac stimulation device 10 in a more realistic setting which thereby reduces the need for testing the device 10 on the patient during or following implantation.

Figure 7A:
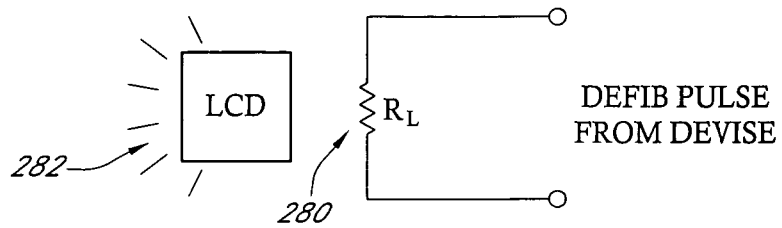
FIGS. 7A-7C illustrate various examples of loads and enunciators that can be incorporated into the patient simulator of FIG. 5.
Figure 7B:
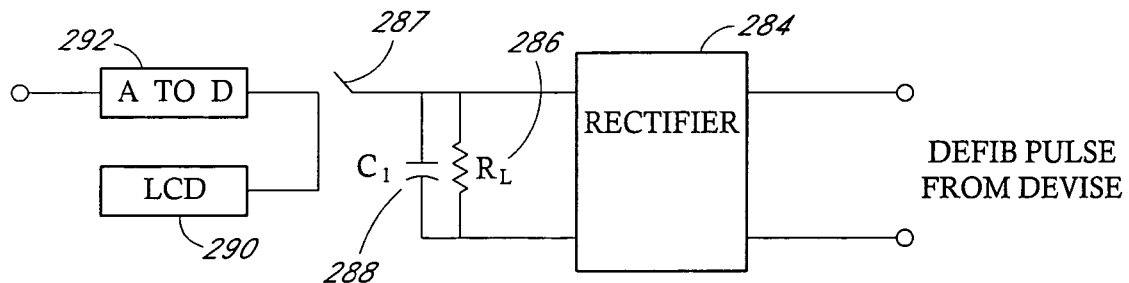
Figure 7C:
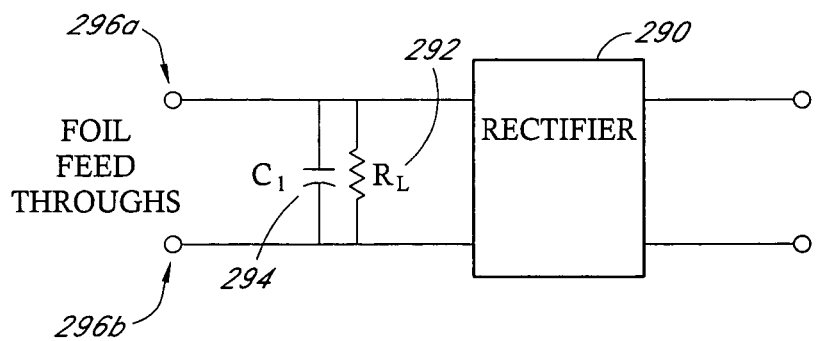

FIGS. 7A-7C illustrate various examples of loads and measurement circuits that can be implemented in the patient simulator 204 of the illustrated embodiment. Referring initially to FIG. 7A, the load may comprise simply a resistor 280 that is positioned proximate to a liquid crystal display (LCD) 282. When the resistor 280 receives a waveform, such as a defibrillation waveform, from the implantable cardiac stimulation device 10, the energy is dissipated through the resistor 280 and the liquid crystal 282 will thereby change color upon registration of the temperature change associated with the resistive heating arising from defibrillation waveform being delivered through the resistor 280. This is a simple embodiment of a measurement circuit 264 that provides a visual indication in the sterile package 202 of the ability of the implantable cardiac stimulation device 10 to deliver a particular waveform. It will be appreciated that the resistor 280 and the LCD 282 could be selected and positioned such that only a waveform having a particular threshold will result in the LCD luminescing. If the LCD 282 fails to luminesce or luminesces weakly, then a person evaluating the efficacy of the implantable cardiac stimulation device 10 will know that this particular device 10 may be unable to deliver a defibrillation waveform with sufficient energy to terminate an arrhythmia.

FIG. 7B illustrates a second embodiment of a load and measurement circuit that measures the amount of energy delivered by an implantable cardiac stimulation device 10 during a defibrillation pulse or waveform. In this embodiment, a rectifier 284 rectifies a biphasic waveform and provides it to a resistor 286 arranged in parallel with a capacitor 288. The voltage on the capacitor 288 will be related to the amplitude and duration of the defibrillation waveform.

Once the waveform is delivered, a switch 287 can then be closed such that the voltage can then be provided to an LCD 290 and an A to D converter 292. The LCD again provides a visual indication of the energy, and the A to D converter 292 provides a further signal quantitatively indicative of the actual energy that has been delivered during the defibrillation pulse. The A to D converter 292 can then send the signal to the microcontroller 250 for subsequent transmission to the test interface device 220 which thereby provides a more specific indication of the amount of energy that can be delivered during a defibrillation waveform by the implantable cardiac stimulation device 10. It will be appreciated that this circuit can also be used to determine the amount of energy delivered by cardioversion waveforms and also by pacing pulses.

FIG. 7C illustrates yet another embodiment of a load and measurement circuit which comprises a rectifier 290 that rectifies a biphasic waveform such as a defibrillation waveform or a cardioversion waveform and provides an output to a resistor 292 arranged in parallel with a capacitor 294. Two contacts 296a and 296b are then attached to the outside of the sterile packaging 202 such that a measuring device can engage with the contacts 296a, 296b and measure the voltage in the capacitor 294. The voltage of the capacitor 294 is again a function of the amplitude duration and energy delivered by the defibrillation or cardioversion waveforms.

Hence, FIGS. 7A-7C illustrate simplified load elements which allow for measurement of the energy that is being delivered during high-voltage waveforms or even during pacing pulses and provide either visual signals or numeric signals indicative of this energy. This information can again be used to ascertain whether the implanted device 10 is suitable for implantation in a particular patient. It will be appreciated from the foregoing that the various embodiments of the present invention provide additional information to the implanting medical professional as to the performance of an implantable medical device 10 prior to implantation. The patient's simulator is able to provide signals to the implanted device 10 which are representative of the signals that the implanted device 10 would see when implanted. Hence the ability of the device 10 to detect the occurrences of conditions requiring medical intervention can be tested prior to implantation. Moreover, the use of multiple loads 272a-272n allows for the implantable medical device 10 to be tested in a number of different configurations that are more representative of the actual conditions that the device 10 would see upon implantation. Each of these characteristics produces the need for testing the implantable medical device 10 on the actual patient and thereby reduces the inherent risk associated therewith.

Although the foregoing description has shown, described and pointed out the fundamental novel features of the invention, it will be understood that various omissions, substitutions, and changes in the form of the detail of the apparatus as illustrated, as well as the uses thereof, may be made by those skilled in the art, without departing from the spirit or the scope of the present invention. Consequently, the scope and spirit of the present invention should not be limited to the foregoing discussion, but should be defined by the appended claims.

What is claimed is:

1. A test assembly for an implantable medical device that senses the function of an organ of a patient when implanted and provides stimulation therapy to the organ in response to the sensed function, the test assembly comprising:

a patient simulator that provides output signals to an implantable medical device wherein the output signals are configured to simulate conditions of the patient requiring the delivery of therapy to the organ of the patient and wherein the patient simulator further includes a measurement component that captures signals indicative of the response of the implantable medical device in response to the output signals for subsequent evaluation of the implantable medical device;

wherein the patient simulator includes a configurable load component such that a plurality of different loads can be coupled to the implantable medical device wherein each of the loads simulate the actual load seen by the implantable medical device following implantation when delivering stimulation therapy to the patient;

wherein the patient simulator further includes a measurement component that provides an indication of the power delivered to the configurable load by the implantable medical device; and wherein the measurement component comprises an LCD that receives power from the configurable load as a result of the stimulation therapy being delivered to the configurable load by the implantable medical device and wherein the LCD illuminates at an intensity proportional to the power delivered to configurable load so as to provide a visual indication of the power of the stimulation therapy delivered by the implantable medical device.

2. A patient simulator assembly for an implantable cardiac stimulation device that has at least one sensor input that receive signals from the heart upon implantation and provides stimulation therapy to the heart via at least one output, the assembly comprising:

a variable load component that receives stimulation therapy from the output of the implantable cardiac stimulation device;

a measurement component that captures signals indicative of the stimulation therapy provided to the variable load component from the implantable cardiac stimulation device such that the signals can be evaluated to assess the ability of the implantable cardiac stimulation device to provide therapeutic stimulation to the patient; and a simulation component that provides simulated signals to the implantable cardiac stimulation device that simulates heart function in a manner that necessitates delivery of therapeutic stimulation to the patient so that the ability of the implantable cardiac device to recognize a condition that requires therapeutic stimulation can be assessed prior to implantation;

wherein the simulation component provides output signals to the implantable medical device that simulates heart function and then captures signals indicative of the response of the implantable medical device to facilitate evaluation of whether the implantable medical device is suitable to moderating abnormal heart function.

3. A simulation assembly for testing, prior to implantation, the ability of an implantable medical stimulation device to deliver therapeutic stimulation to an organ of a patient in response to sensed conditions of the organ, the assembly comprising:

load means for receiving stimulation therapy from the output of the implantable cardiac stimulation device;

measurement means for measuring at least one parameter of the therapeutic stimulation provided to the load means by the implantable medical device; and simulation means for providing signals to the implantable cardiac stimulation device that simulate the organ in a manner that necessitates delivery of therapeutic stimulation from the implantable medical device;

wherein the measurement means comprises an LCD that receives power from the therapeutic stimulation and illuminates substantially proportionately to the power received.

4. A test assembly for an implantable medical device that senses the function of an organ of a patient when implanted and provides stimulation therapy to the organ in response to the sensed function, the test assembly comprising:

a patient simulator that provides output signals to an implantable medical device wherein the output signals are configured to simulate conditions of the patient requiring the delivery of therapy to the organ of the patient and wherein the patient simulator further includes a measurement component that captures signals indicative of the response of the implantable medical device in response to the output signals for subsequent evaluation of the implantable medical device;

wherein the patient simulator provides output signals to the implantable medical device that simulates heart function and then captures signals indicative of the response of the implantable medical device to facilitate evaluation of whether the implantable medical device is suitable to moderating abnormal heart function.

5. The assembly of claim 4, wherein the test assembly further comprises a sterile barrier that encompasses the implantable medical device and the patient simulator such that the implantable medical device can be tested prior to implantation with reduced risk of contamination of the implantable medical device.

6. The assembly of claim 5, further comprising a communications interface that permits communication through the sterile barrier between the patient simulator and a test interface device to thereby allow for the captured signals to be transmitted outside of the sterile barrier.

7. The assembly of claim 6, wherein the communications interface comprises telemetry interface.

8. The assembly of claim 6, wherein the communications interface comprises a hardwired interface with at least one exposed contact on the outer surface of the sterile barrier.

9. The assembly of claim 4, wherein the patient simulator includes a configurable load component such that a plurality of different loads can be coupled to the implantable medical device wherein each of the loads simulate the actual load seen by the implantable medical device following implantation when delivering stimulation therapy to the patient.

10. The assembly of claim 9, wherein the configurable load component includes resistive and capacitive components so as to more accurately simulate the load of the organ of the patient.

11. The assembly of claim 9, wherein the patient simulator further includes a measurement component that provides an indication of the power delivered to the configurable load by the implantable medical device.

12. The assembly of claim 11, wherein the measurement component samples the stimulation therapy being delivered to the configurable load and produces a signal indicative of the stimulation therapy.

13. A simulation assembly for testing, prior to implantation, the ability of an implantable medical stimulation device to deliver therapeutic stimulation to an organ of a patient in response to sensed conditions of the organ, the assembly comprising:

load means for receiving stimulation therapy from the output of the implantable cardiac stimulation device;

measurement means for measuring at least one parameter of the therapeutic stimulation provided to the load means by the implantable medical device; and simulation means for providing signals to the implantable cardiac stimulation device that simulate the organ in a manner that necessitates delivery of therapeutic stimulation from the implantable medical device;

wherein the simulation means comprises a signal generator that provides output signals to an input of the implantable medical device that simulates a condition of the organ that necessitates the delivery of therapeutic stimulation to the organ from the implantable medical device.

14. The assembly of claim 13, wherein the load means comprises a variable load component that can be varied to simulate different loads that the implantable medical device will see when delivering therapy following implantation.

15. The assembly of claim 14, wherein the load means comprises a plurality of loads and a selectable gate such that a particular load can be selected to simulate the delivery of therapeutic stimulation to a particular location of the organ.

16. The assembly of claim 13, wherein the measurement means comprises a measurement circuit that samples the waveform of the therapeutic stimulation.

17. The assembly of claim 13, further comprising a communication means for communicating between the simulation assembly and an external programming device.

18. The assembly of claim 17, wherein the communication means comprises a telemetry transceiver that communicates with the external programming device via RF signals.

* * * * *